United States Patent [19]

Foux

[11] Patent Number: 4,943,292

[45] Date of Patent: Jul. 24, 1990

[54] PLATE FOR BROKEN BONE FIXATION

[75] Inventor: Amnon Foux, Haifa, Israel

[73] Assignee: National Research Council of Canada, Ottawa, Canada

[21] Appl. No.: 433,144

[22] Filed: Nov. 8, 1989

[51] Int. Cl.⁵ .............................................. A61B 17/58
[52] U.S. Cl. ......................................... 606/70; 606/69
[58] Field of Search .................................. 606/69–71; 128/92 YP, 92 YL

[56] References Cited

U.S. PATENT DOCUMENTS

| Re. 28,241 | 6/1976  | Allgower et al. | 606/69 |
|------------|---------|-----------------|--------|
| Re. 31,628 | 7/1984  | Allgower et al. | 606/69 |
| 2,486,303  | 10/1949 | Longfellow      | 606/71 |
| 3,596,656  | 8/1971  | Kaute           | 606/71 |
| 3,779,240  | 12/1973 | Kondo           | 606/69 |
| 4,297,993  | 11/1981 | Harle           | 606/70 |
| 4,338,926  | 7/1982  | Kummer et al.   | 606/70 |
| 4,408,601  | 10/1983 | Wenk            | 606/69 |
| 4,524,765  | 6/1985  | de Zbikowski    | 606/69 |

FOREIGN PATENT DOCUMENTS

| 1505513 | 12/1967 | France         | 128/92 YP |
| 959771  | 9/1982  | U.S.S.R.       | 128/92 YL |
| 1173480 | 12/1969 | United Kingdom | 128/92 YP |

Primary Examiner—Robert A. Hafer
Assistant Examiner—Kevin G. Rooney
Attorney, Agent, or Firm—John F. Leman

[57] ABSTRACT

An implantable plate for joining together two pieces of a broken bone is formed to have a plurality of elongated holes for the screws that fasten the plate to the bone on both sides of the fracture. The screws are positioned at the end of the elongated hole that is farthest from the fracture. The portion of each elongated hole that is not occupied by the screw is filled with a cushion of elastic material that may be deformed elastically when the screw shank is pressed against it, thereby allowing lateral movement of the screw in the hole. When the plate is implanted in the body of a person and fastened to a fractured bone by means of screws through the elongated holes, the plate stabilizes the bone pieces but permits the screws, and hence the bone pieces, to move a short distance back and forth in the direction of the axis of the bone in order to promote healing.

13 Claims, 2 Drawing Sheets

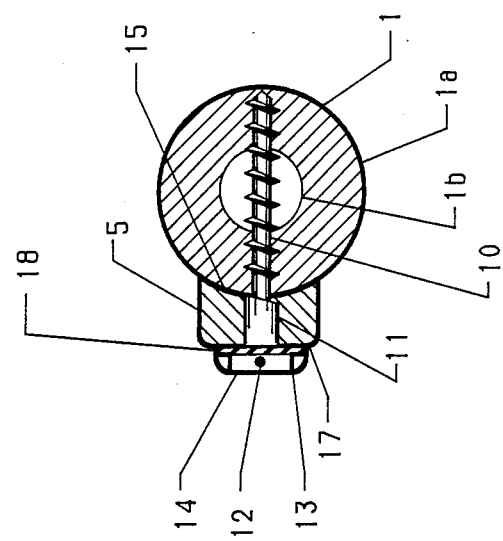
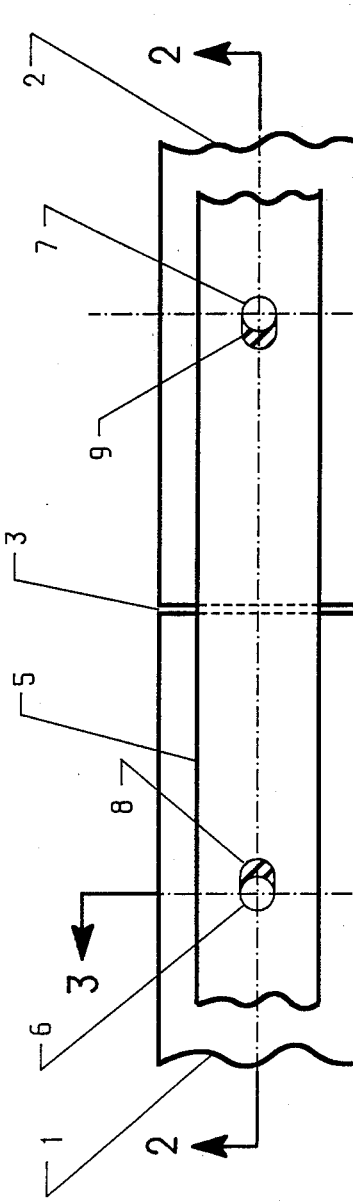
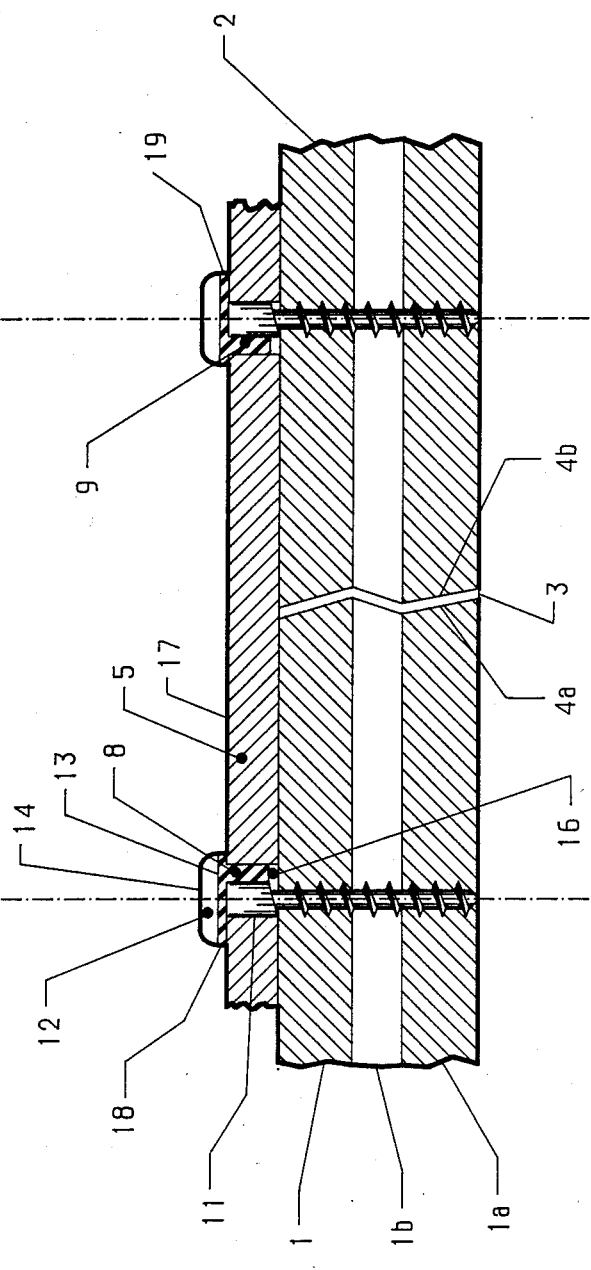

PLATE FOR BROKEN BONE FIXATION

BACKGROUND OF THE INVENTION

1. Field of the Invention

The invention relates to internal bone fixation plates which are used by surgeons to hold together broken bones so as to facilitate healing of the bone.

2. Description of the Prior Art

The development of implantable plates for internal fixation of fractured long bones was first introduced late in the nineteenth century. The basic concept is to place a plate in contact with the bone so that the plate spans the fracture, and to fasten the plate to the bone on both sides of the fracture by means of screws. The plate and the screws must, of course, be made of materials that will not cause adverse reactions in the body and that will not deteriorate in any reasonable time. Internal fixation plates are clinically appealing because they produce the significant advantages of a rapid return of functional weight bearing, improved rehabilitation of surrounding soft tissues, and shortened hospital stay.

Fundamental changes in the concept of fracture fixation took place in 1946 with the introduction of compression plates. These plates load the bone in compression at the time of fixation. Such plates are often very rigid, and rigidity deprives the bone of normal stresses. The lack of stresses results in loss of bone mass and local weakening of the cortex of the bone, which is the bone's outer wall. It also restricts load-induced deformations at the fracture site, which inhibits the healing process by restricting the exchange of liquids via the canaliculi. The exchange of liquids is important for the nutrition of the osteocytes.

An important unfavourable effect of rigid fixation is the suppression of the osteogenic potential of the periosteum during the healing phase, so that limited or no external callus develops around the fracture. This makes radiologic assessment of the state of union of a fracture impossible. It also delays the process of union, since the healing has to rely mostly on the direct growth of the Haversian envelope across the fracture. During the phase of remodelling, the fact that the plate bears most of the load leads the loss of beneficial structural alignment of newly-formed osteons and lamellae, and thus to a weak union.

Delayed union and loss of bone mass and structure have led to refractures after removal of the plate. No objective criteria exist to define the best time to remove these devices, which are designed to fulfil a temporary function. Too-early removal might cause a refracture due to incomplete healing, and too-late removal might cause a refracture due to weakening of the bone under the plate.

Various plates to hold the broken bone in a good position for healing while reducing the rigidity of fixation and the shielding from stress have been tried and are well known in the art. The previous method of achieving this goal was by making the plates of a material having a lower modulus of elasticity, or by reducing their cross section. However, reduction of plate rigidity by such methods affects the axial, bending and torsional stiffnesses, and this is in opposition to the basic immediate need of holding the broken portions of the bone in their desired relative position while also permitting the bone to endure axial stress. The dilemma in the design of bone fixation plates is in the need to maintain very great stability of the relative positions of the broken pieces of bone, for which high bending and torsional stiffnesses are needed, while at the same time to allow axial loading of the bone, for which low axial stiffness is needed.

SUMMARY OF THE INVENTION

By the present invention there is provided a device adapted for placement in the body of a person to span a fracture in a bone and to be connected by means of screws to the bone on both sides of the fracture, comprising a plate, cushions, and screws, all constructed of biologically-compatible material, in which:

said plate is substantially rigid;

said plate is provided with a plurality of holes that enable passage of said screws through said plate such that the central axis of each of said screws lies approximately in a plane that contains the long axis of the bone and is nearly perpendicular to said long axis when the device is installed;

at least all those holes which are on one side of the fracture when the device is installed are elongated in a direction substantially parallel to the long axis of the bone when the device is installed;

each hole which is an elongated hole is partially filled with a said cushion which is an elastic biologically-compatible material positioned with a snug fit in the portion of said elongated hole which is to be closer to the fracture when the device is installed, said cushion being of a shape and material that permits one of said screws to pass through the unfilled portion of said elongated hole for the purpose of fastening the device to the bone.

It is an object of the present invention to provide an implantable plate for broken bone fixation which will allow a small amount of movement of the broken pieces of the bone in the direction of the long axis of the bone only, thereby stimulating healing, while holding the pieces of the bone quite rigid with respect to shearing, torsional and bending movements.

The foregoing and other objects of the present invention are attained by a system comprising a rigid plate, elastic cushions, low-friction washers, and screws with conventional bone thread.

The term "elastic", as used herein, describes a solid material which responds to pressure by temporarily deforming in the sense of reducing its dimension in the direction of the applied pressure. The material may or may not simultaneously expand in another direction. When the pressure is removed, the material returns to essentially the same dimensions which it had before the pressure was applied.

In the preferred embodiment, the plate will be longer in the direction substantially parallel to the long axis of the bone when the plate is installed. In the descriptions herein, the plate will be assumed to have (i) a long dimension that is intended to lie substantially parallel to the long axis of the bone and is called the "length", (ii) a smaller dimension that is perpendicular to the length and will be tangential to the surface of the bone when the plate is installed, and is called the "width", and (iii) a third dimension, usually the smallest of the three, that is orthogonal to the other two and is called the "thickness".

The terms length, width and thickness are used herein for convenience. It must be understood, however, that an embodiment of the present invention could have a different shape for special needs in relation to certain fractured bones, and nevertheless the principles of the present invention would apply.

The plate is substantially rigid and is provided with a plurality of holes that have their axes in the direction of the thickness and are elongated in the direction of the length of the plate. The plate is sufficiently long to span a fracture and to be connected to the bone on both sides of the fracture by means of screws passing through the elongated holes. Each screw passing through an elongated hole has a round shank which fits snugly in the narrowest width of the elongated hole, and is positioned at the end of the elongated hole which is farther from the fracture. The portion of the elongated hole between the screw and the end of the elongated hole which is closer to the fracture is filled with a cushion made of elastic material. The screws can move laterally within the hole a small distance towards the fracture by deforming the elastic cushion.

The elastic cushion has a shape that, in the plane of plate, is approximately described as being bounded by two equal semi-circles facing the same direction and two parallel lines tangent to the said semi-circles and also parallel to the line joining the centres of the two semi-circles. The dimension in the direction perpendicular to this plane, which is the direction of the thickness of the plate, is usually uniform. The method of making the cushion can be any suitable method known in the art.

The head of each screw may be separated from the plate by a flat washer made of a material having a low coefficient of friction, so that the head of the screw will not bind on the plate and the movement of the screw will be facilitated.

The amount of elongation of a hole can be described in terms of the distance between the centres of the two largest circles that would fit in the hole at opposite ends of the hole. In many cases, both ends of the elongated hole are semi-circular; the end containing the cushion could be any shape, but the end containing the screw should conform approximately to the shape of the screw. The amount of elongation is usually a few millimeters, but the elongation in any particular case depends on various considerations, especially the desired amount of axial movement and the compressibility of the cushion. The direction of the elongation is always in the direction of desired axial movement of the broken bone.

There is no known reason for making the elongation of any hole in a plate different from that of any other hole in a plate, but the present invention is not limited to plates in which all holes have the same size. All the holes in a plate will be elongated in the same direction. The methods of making the plate with the elongated holes can be any suitable method known in the art.

When the plate is implanted on a fractured bone, the axial compression loads that may act on the bone are transmitted through the screws to the elastic cushions, which are thereby temporarily deformed as the screws, along with the bone, move a small distance towards the fracture. The amount of elongation of the holes and hence the size of the cushions, the modulus of elasticity of the cushion, and the number of screws in elongated holes are the principal determinants of the amount of relative movement of the bone sections at the fracture. It must be understood, however, that an embodiment of the present invention could have cushions of different material, shape and thickness for needs in relation to the amount of relative motion of fractured bone sections, and nevertheless the principles of the present invention would apply.

The method of preparing the bone, using bone drills and taps, and attaching the plate to the bone, are not significantly different with the present invention than with any bone fracture fixation plate known in the art.

The surgeon who implants the plate will lay open the surrounding tissue to expose as much of the bone as required, and will then position the pieces of broken bone by clamping them to a rigid template so that the fractured ends line up and the bone is restored as nearly as possible to the configuration which it had before the fracture occurred. Various clamps well known in the art can be used to hold the bone in the desired position. The surgeon will then drill holes in the bone to receive the screws, using holes in the template which position the drill so as to correctly space and align the holes. The template and clamps are then removed, and the holes in the bone are commonly tapped to produce an internal thread that will match the thread of the screw.

The surgeon will position the plate, with the cushions inserted in the elongated holes, against the bone and insert the screws through the washers and through the plate so as to fasten the plate to the bone. Usually, care is taken to ensure that the screws are tightened with an equal torque.

There is no requirement with the present invention to separate the fractured ends of the bone by any distance, but neither is it desirable to force the fractured ends firmly together. The surgeon, with experience, might find that it is advisable to introduce some small amount of separation of the fractured ends, but this separation would always be less than the elongation of the holes.

The number of elongated holes depends on the size of the plate, which in turn depends on the size of the bone and the nature of the fracture that is to be fixed by the plate. The positioning of the plate is a matter for the judgement of the surgeon, and a variety of plates of different sizes and with different numbers of holes could be offered to the surgeon to suit different cases. It is essential to have at least two screws on each side of the fracture, to prevent the section of the broken bone from pivoting about the screw as could happen if there is only one screw on one side of the fracture. It is highly desirable to have at least three screws on each side of the fracture, because that arrangement is safer.

A typical plate for use on a fractured long bone of the leg or arm would have much greater length than width, and would have at least six collinear elongated holes that would be placed so that at least three elongated holes were on each side of the fracture.

It is conceivable that in certain cases, where the piece of bone on one side of the fracture is small or oddly shaped, the holes in the plate on that side of the fracture should not be elongated and provided with a cushion but should be round like conventional holes in a bone fixation plate. In such a case, there is no requirement that the round holes be arrayed in straight lines parallel to the length of the plate.

It is also conceivable that there could be, in the region of the principal fracture, additional pieces of bone which should be held in place so as to allow them to re-attach themselves to the bone, but which should not move during the healing process. The plate could be provided with conventional holes, in additional to the elongated holes, and screws could be placed in the conventional holes for the purpose of securing such additional pieces of bone in a desired position.

It is further conceivable that large plates for large bones might have the elongated holes arranged in two or more parallel lines substantially parallel to the long axis of the bone when the plate is installed, or in some other useful pattern. Such a plate is likely to be curved to conform to the outer surface of the bone.

In all cases, the cushion is placed at the end of the elongated hole which is closer to the fracture. Therefore, on opposite sides of the fracture, the cushion will be at opposite ends of the elongated holes. When the plate and screws are first installed, and when the body is at rest, the screws will be fully towards the uncushioned end of the elongated holes. When external forces on the broken bone tend to push the fractured ends together, a small amount of movement in that sense will occur, as the screws which are firmly fastened to the bone slide in the elongated hole and in so doing deform the elastic cushion. When external forces on the broken bone tend to pull the fractured ends apart, the screws will not move from the rest position because they are at the rigid end of the elongated hole. Any force which might tend to rotate the pieces of bone around the long axis of the bone has no effect on the fracture, because the shank of the screw fits snugly in the elongated hole in the direction perpendicular to the long axis of the bone. Any force which might tend to bend the bone transversely to its long axis has no effect on the fracture, because the heads of the screws hold the bone firmly to the rigid plate and because the shank of the screw fits snugly in the elongated hole so as to prevent movement in the direction that is the width of the plate.

The cushion must, of course, be a substance that is biologically compatible, which means that it must not cause adverse reactions in the body and must not deteriorate for a reasonable time. Numerous plastics are known to have such properties, and examples of substances suitable for the present invention are "teflon" and polymethylmethacrylate. The cushion could also be made of natural or synthetic bone, and in that case the cushion would not simply be an inert part of the invention but would eventually merge with the pieces of broken bone. For the purpose of the present invention, the elasticity of the cushion is an important parameter. Clinical experience will determine the optimal choice of material for the cushion, which might be different for different types of fractures, different bones of the body, and different people. It is known, however, that high elasticity such as is characteristic of latex for example, will not be appropriate. The elasticity that is characteristic of "nylon" is an example of the appropriate range. The chosen material must also have the characteristic of quickly restoring itself to approximately its original shape and size when the deforming force is removed.

When the screws slide in the elongated holes and deform the cushions in the direction of the long axis of the bone, the cushions will tend to temporarily expand in a perpendicular direction to compensate for the deformation. To allow for this distortion of the cushion, it is desirable that the cushions be slightly smaller than the thickness of the plate.

The plate and the screws must not cause adverse reactions in the body and must not deteriorate for a reasonable time. Various materials with such properties are known and used in other types of bone fixation plates. The material of the plate is chosen for high rigidity, and may be stainless steel. The material of the screws is chosen as for typical surgical screws, and may be stainless steel.

The screws in the present invention must be able to slide a short distance in the elongated hole back and forth in the direction of the elongation, and hence the heads of the screws must not bind against the plate and must not be shaped so as to be rigidly confined in the elongated hole. To facilitate the sliding motion of the screws, a washer of low-friction material may be inserted between the head of the screw and the plate. In one embodiment of the invention, this washer and the cushion at the end of the elongated hole are integral parts of the same thing, although they are not necessarily made of the same material. The screws required for this invention usually have a flat-bottomed head to conform to the usual flat-topped surface of the plate. This is uncommon in surgical screws, because an object of most existing bone fixation plates and accompanying screws is to fasten the bone to the plate in a manner which allows absolutely no movement. An alternative embodiment of the present invention would use conically or spherically tapered screw heads which conform to tapered sockets in the washers through which the screws pass, but experience and intuition indicate that the preferred embodiment, and the simplest, uses screw heads with flat bottoms.

The screws must be installed so that they all are very nearly parallel to each other, because the sides of the elongated holes in the plate are all parallel. If the screws are not substantially parallel to the sides of the elongated holes, they will bind against the sides of the elongated holes so as to prevent or limit the sliding of the screws.

The side of the plate adjacent to the bone may be somewhat concave in order to conform to the approximately round outer surface of the bone. The desired degree of concavity depends on the diameter of the bone.

The side of the plate adjacent to the bone may be made to have ridges, which may be called rails, running parallel to the longest direction of the plate. This facilitates the sliding of the plate against the bone in the direction of the axis of the bone.

In all cases, the surface of the plate on the side adjacent to the bone must be smooth to facilitate the sliding of the bone on the plate. In one embodiment of the invention, this surface may be coated with a thin layer of a material having a low coefficient of friction. Various materials with that property are known in the art, but the chosen material must not cause adverse reactions in the body and must not deteriorate for a reasonable time. "Teflon" is one such material. In another embodiment of the invention, a thin strip of low-friction material is placed between the plate and the bone when the bone is installed.

The surface on the side of the plate away from the bone must be flat and smooth, at least in the regions close to each of the elongated holes. In one embodiment of the invention, to facilitate the sliding on the plate of the washers through which the screws pass, this surface is coated with a layer of low-friction material.

In an alternative embodiment of the invention, the axes of all the screws passing through the elongated holes in the plate nearly intersect the long axis of the bone but are not perpendicular to it. The axes of all screws on the same side of the fracture would typically be nearly parallel to each other, but not parallel to the axes of the screws on the other side of the fracture. The sides of each elongated hole are defined by a surface traced by a straight line moving parallel to the axis of the screw passing through that hole when the plate is installed. The portion of the elongated hole between the screw and the end of the elongated hole which is closest to the fracture is filled with an appropriately shaped cushion. The appropriate shape for the cushion includes sides that will be parallel to the axis of the screw when other sides are parallel to the surface of the plate. The head of each screw is separated from the plate by a wedge-shaped washer made of a material having a low coefficient of friction and positioned so that one wedge side is perpendicular to the axis of the screw passing through the wedge-shaped washer and the other wedge side is parallel to the surface of the plate which is away from the bone.

The top of the screw head, containing the recess by which the screw driving tool engages the screw, can be any convenient shape. The recess in the top of the screw head by which the screw driving tool engages the screw can be any design that conforms to a screw driving tool, but for convenience would conform to standard screw driving tools so that a special screw driving tool is not required for the present invention.

The surgeon who installs the plate will usually drill and tap holes in the bone to receive the screws. These holes must, of course, be properly positioned to align with the pre-existing holes in the plate. These holes must also be nearly parallel to the axes of the holes in the plate when the plate is installed, or the screws will not be positioned as they are required to be. It would be inadvisable to drill the holes in the bone using the plate as a guide for two reasons: first because the drill would be likely to damage the sides of the holes in the plate, and the cushion if it is already in place, and second because elongated holes are not a reliable drilling guide.

Accordingly, a template for drilling the holes in the bone will normally be provided with the plate. The template must, of course, correspond to the particular plate. The template would have drill guides with round holes rather than elongated holes. The round holes in the template must be spaced so that they align with the particular ends of the holes in the plate that are not the ends containing the cushion. The drill guides should also be designed to ensure that the holes drilled through them would be aligned with the axis of each screw passing through the elongated hole in the corresponding bone plate when the plate is installed.

An alternative embodiment of the invention uses a plate in which the narrowest width of each elongated hole, and thus of the cushion, is slightly larger than the diameter of the shank of the screw in that hole. In this embodiment, the cushion extends to all sides of the elongated hole and contains a substantially round hole for the screw in which the screw fits snugly and which is towards the end of the elongated hole farther from the fracture so that the amount of motion possible by deforming the part of the cushion farther from the fracture is small and is not inconsistent with the desire to allow a small amount of movement back and forth in the direction of the long axis of the bone. The size of the screw is not much smaller than the narrowest width of the elongated hole and the cushion is not highly elastic, so that the amount of movement which is possible in the direction transverse to the plate and to the long axis of the bone is small and is not inconsistent with the desire for substantial rigidity in all directions except the direction of the long axis of the bone. The possibility of a limited amount of flexural flexibility, in addition to the axial flexibility, may be desired by the surgeon in particular cases.

A possible disadvantage of the embodiment last mentioned is that the parts of the cushioning material on the sides of the elongated hole and at the end of the elongated hole farther from the fracture have a risk of deteriorating and breaking under the pressure of use because they are relatively thin, and in particular are thinner than the principal part of the cushion. Accordingly, it is especially important in this embodiment to use material that is strong as well as being elastic and biologically compatible.

BRIEF DESCRIPTION OF THE DRAWINGS

The above and other objects, features and advantages of the present invention will become apparent from a consideration of the following detailed description presented in connection with the accompanying drawing.

FIG. 1 shows a part of a fractured bone and a part of the plate, including two elongated holes only, spanning the fracture.

FIG. 2 shows a longitudinal section of the same portion of the fractured bone and plate as viewed by a section along the line A—A in FIG. 1.

FIG. 3 shows a cross-section of the same portion of the fractured bone and plate as viewed by a section along the line B—B in FIG. 1.

DETAILED DESCRIPTION OF PREFERRED EMBODIMENTS

Figure 5:
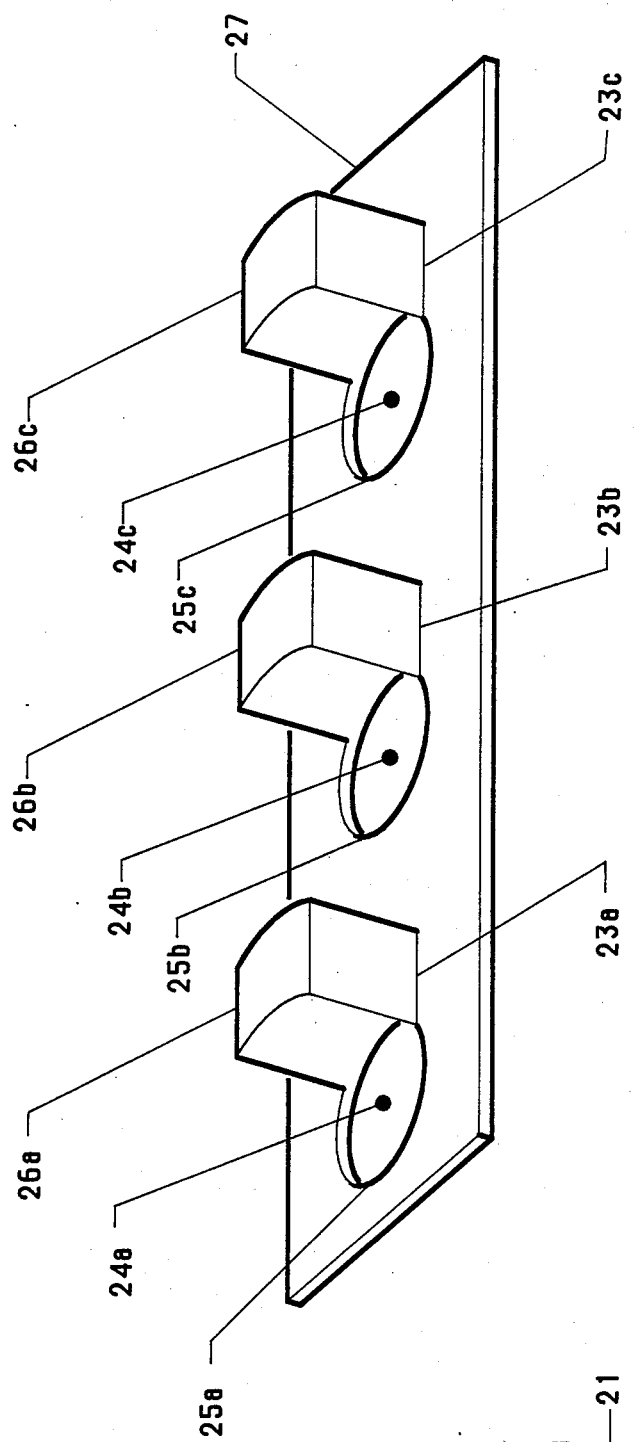
FIG. 5 shows a longitudinal section of a strip of material that fulfils the functions of several washers and includes the cushions for several elongated holes as integral parts of the strip.

FIGS. 1 to 3 show a portion of a bone which has been broken into two pieces 1 and 2 at the fracture 3. A typical bone consists of an inner marrow 1b and an outer shell 1a. The objective of medical treatment is to facilitate the union of the two fracture surfaces, 4a and 4b. The distance between the surfaces 4a and 4b is minimal, possibly nothing and not likely greater than 1 millimeter. The plate, , which is a principal component of the present invention and of which only part is shown, spans the fracture 3. The elongated holes 6 and s contain screws which are not shown in FIG. 1. The ends of the elongated hole nearer to the fracture contain the cushions 8 and 9. The sides of the elongated holes 6 and s are perpendicular to the top surface 17 of the plate 5, and the same is true for all holes.

FIG. 2 and 3 show the screws in more detail. Each screw has a threaded portion 10, an unthreaded shank 11 in the form of a right circular cylinder with sides at least as long as the thickness of the plate, and a head 12. The head is bounded on the bottom by a flat surface 13, and on the top 14 by any suitable surface such as the flat top with rounded edges that is shown. The top of the head contains a recess, not shown, designed to engage a standard surgical screw driving tool, which commonly requires an essentially hexagonal recess.

FIGS. 2 and 3 show the washer 18 which facilitates the sliding of the bottom surface 13 of the screw head 12 over the top surface 17 of the plate 5, where the term top surface refers to the surface of the plate furthest away from the bone. The same situation obtains for the washer 19 and all other washers related to elongated holes.

FIG. 2 shows, looking for example to the left of the fracture 3 only, that the cushion 8 does not extend above the plate 5 on the side away from the bone piece 1. Neither does the cushion 8 extend below the plate 5 on the side adjacent to the bone piece 1, and furthermore it is desirable that a small space 16 be left between the cushion and the bone to permit expansion of the cushion as a result of the deformation that occurs repeatedly in normal use. The cushion s must be held in its position by the combination of the washer 18 and the screw head 12. That consideration dictates a minimum size of the washer 18 and the screw head 12. Moreover, the minimum size of the washer 18 and the screw head 12 should be such that no part of either of their edges on the side nearest to the plate 5 will ever fall within the edge of the elongated hole 6.

FIG. 3 shows the screw inserted in a typical fashion, which is to pass all the way through the bone but not extend significantly beyond it. The length of screws is chosen appropriately for each case. The surface of the plate adjacent to the bone, which may be called the bottom surface 15, of the plate 5 is represented in FIG. 3 as conforming very closely to the bone piece 1, but such very close conformity is not essential.

Figure 4:
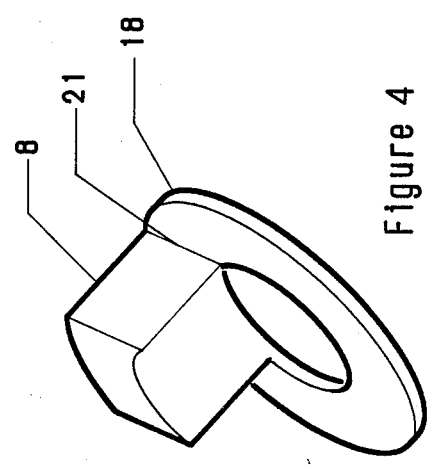
FIG. 4 shows a washer having the cushion as an integral part of it.

FIG. 4 shows an embodiment in which the cushion 8 is an integral part of the washer 18. The washer 18 and the cushion 8 may be made of the same material. Alternatively, a material chosen for the desired elasticity of the cushion and another best suited for the purpose of the washer may be joined together at the contact surface 21.

FIG. 5 shows an alternative embodiment of the cushion which provides a single strip 27 of suitable material that fulfils the function of several washers, such as washer 18 and all other washers for all other elongated holes (not shown) on the same side of the fracture 3. The strip 27 contains round holes 24a, 24b and 24c which are spaced so that the ends 25a, 25b and 25c of those holes will align with the ends of the elongated holes exemplified by hole 7 which are the ends farthest from the fracture 3 when the plate 5 is installed. The strip 27 bears the cushions 26a, 26b and 26c which will fit into the elongated holes exemplified by hole 7 on the plate 5 at the ends nearest to the fracture 3. The cushions 26a, 26b and 26c, are integral parts of the strip 27 and are either made of the same material as the strip 27 or are a dissimilar material joined to it at the contact surfaces 23a, 23b and 23c.

The strip 27 could extend for the length of that portion of the plate which is on one side of the fracture 3. Another strip on the other side of the fracture 3 would fulfil the functions of washer 19, cushion 9 and other cushions and washers (not shown) on that side of the fracture 3. The two strips may be identical but must be installed so that the cushions are on the side of the elongated hole nearer to the fracture. In order that the strips on opposite sides of the fracture 3 act like washers and independently slide back and forth in the direction allowed by the elongated holes 6 and 7 and similar holes, at least one separate strip is required on each side of the fracture 3 and the strips on opposite sides of the fracture 3 must not touch each other when they have both slid as far as possible in the direction that deforms the cushions.

In yet another embodiment, a small part of the material of the cushion surrounds the screws on all sides that are not in contact with the principal cushion. In this embodiment, the narrowest widths of the elongated holes, and thus of the cushions, are slightly larger than the diameter of the shanks of the screws, but the screws fit snugly into a substantially round hole in the cushioning material.

An alternative embodiment uses screws having tapered shanks which decrease in circumference at points farther away from the head of the screw, and the sides of the elongated holes and the sides of the cushions, which are in contact with the shanks of the screws, are tapered to match the taper of the shanks of the screws.

Other embodiments have a plate that has round holes without cushions on one side of the fracture, or have more than one line of elongated holes, but all elongated holes must be elongated parallel to the long axis of the bone.

It is to be understood that the above-described embodiments are only illustrative of the application of the principles of the present invention. Numerous other modifications and alternative arrangements may be devised by those skilled in the art without departing from the spirit and scope of the present invention, and the appended claims are intended to cover such modifications and arrangements.

I claim:

1. A device adapted for placement in the body of a person to span a fracture in a bone and to be connected by means of screws to the bone on both sides of the fracture, comprising a plate, cushions, and screws, all constructed of biologically-compatible material, in which:

said plate is substantially rigid;

said plate is provided with a plurality of holes that enable passage of said screws through said plate such that the central axis of each of said screws lies approximately in a plane that contains the long axis of the bone and is nearly perpendicular to said long axis when the device is installed;

at least all those holes which are on one side of the fracture when the device is installed are elongated in a direction substantially parallel to the long axis of the bone when the device is installed;

each hole which is an elongated hole is partially filled with a said cushion which is an elastic biologically-compatible material positioned with a snug fit in the portion of said elongated hole which is to be closer to the fracture when the device is installed, said cushion being of a shape and material that permits one of said screws to pass through the unfilled portion of said elongated hole for the purpose of fastening the device to the bone.

2. A device as defined in claim 1 in which one or more of said screws are provided with a washer installed between the head of said screws and the surface of said plate, said washer being made of a material having a low coefficient of friction.

3. A device as defined in claim 2 in which said washer is an integral part of said cushion.

4. A device as defined in claim 2 in which more than one of said washers comprise a strip that is long enough to completely span more than one of said elongated holes, said strip being provided with holes spaced to match said elongated holes so that said screws pass through said holes in the strip as well as said elongated holes.

5. A device as defined in claim 4 in which said cushion in more than one of said elongated holes is an integral part of, and projects outwards from, said strip.

6. A device as defined in claim 1 in which all the holes are elongated holes and all are provided with said cushions.

7. A device as defined in claim 1 in which said cushion is an integral part of said plate.

8. A device as defined in claim 1 in which said cushion is made of natural or artificial bone.

9. A device as defined in claim 1 in which the surface of said plate that is farthest from the bone is essentially flat.

10. A device as defined in claim 1 in which the surface of said plate that is adjacent to the bone is concave.

11. A device as defined in claim 1 in which the surface of said plate that is adjacent to the bone is railed.

12. A device as defined in claim 1 in which the same material that comprises said cushion extends to all sides of said elongated hole, with the greatest part of said material being towards the end of said elongated hole which is to be closer to the fracture when the device is installed, said screw having a shank that fits snugly across the narrowest width of said elongated hole allowing for the partial filling of the narrowest width by the cushion material.

13. A device as defined in claim 2 wherein said central axis of each of said elongated holes on one side of the fracture when the device is installed is not perpendicular to said long axis of the bone, and wherein each of said washers has non-parallel flat sides such that one of said flat sides is perpendicular to said central axis of said elongated hole and the other said flat side is parallel to the surface of said plate farthest from the bone.

* * * * *